(12) United States Patent
Matusch

(10) Patent No.: US 8,333,730 B2
(45) Date of Patent: Dec. 18, 2012

(54) SINGLE-USE INJECTOR HAVING A FLEXURALLY ELASTIC METAL HOUSING

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 22 days.

(21) Appl. No.: 13/134,720

(22) Filed: Jun. 15, 2011

(65) Prior Publication Data

US 2011/0251550 A1    Oct. 13, 2011

Related U.S. Application Data

(63) Continuation-in-part of application No. PCT/EP2009/008612, filed on Dec. 3, 2009.

(30) Foreign Application Priority Data

Dec. 18, 2008  (DE) .................. 10 2008 063 519

(51) Int. Cl.
*A61M 5/30* (2006.01)
(52) U.S. Cl. ........................................ 604/68
(58) Field of Classification Search .............. 604/68
See application file for complete search history.

(56) References Cited

U.S. PATENT DOCUMENTS

| | | | |
|---|---|---|---|
| 3,094,989 A | 6/1963 | Staufer | |
| 3,557,784 A | 1/1971 | Shields | |
| 5,681,291 A | 10/1997 | Galli | |
| 6,793,646 B1 * | 9/2004 | Giambattista et al. | 604/90 |
| 2001/0039394 A1 | 11/2001 | Weston | |
| 2001/0051789 A1 | 12/2001 | Parsons | |
| 2005/0020984 A1 | 1/2005 | Lesch, Jr. | |
| 2006/0189938 A1 * | 8/2006 | Hommann et al. | 604/137 |
| 2006/0264830 A1 | 11/2006 | Hommann | |
| 2009/0281496 A1 | 11/2009 | Matusch | |
| 2010/0076373 A1 | 3/2010 | Matusch | |
| 2010/0106090 A1 | 4/2010 | Matusch | |

FOREIGN PATENT DOCUMENTS

| | | |
|---|---|---|
| EP | 0 518 416 A1 | 12/1992 |
| GB | 805 184 A | 12/1958 |
| GB | 805184 | 12/1958 |
| GB | 805184 A | 12/1958 |
| WO | WO 9624398 A1 | 8/1996 |
| WO | WO 00/62846 | 10/2000 |
| WO | WO 2005/070481 | 8/2005 |

* cited by examiner

*Primary Examiner* — Nicholas Lucchesi
*Assistant Examiner* — Jason Flick
(74) *Attorney, Agent, or Firm* — R. S. Lombard; K. Bach

(57) ABSTRACT

A single-use injector comprising a housing (200) accommodating a mechanical spring energy reservoir (50), a cylinder/piston unit (100), a piston-actuating ram (60) and a trigger unit (80), the spring-loaded piston-actuating ram being supported on the housing via support rods (240) or draw hooks (250) and each contact zone between an individual support rod or draw hook and the piston-actuating ram representing a wedge gear pairing that forces the respective support rod or draw hook radially outwards. The housing of the injector consists of a thin-walled sheet metal part. Said sheet metal part has at least two limbs (220, 250) arranged parallel to each other. The sheet metal part has at least two pressure bars or at least two draw hooks the free ends of which are bent in an angular fashion to define a supporting section for the piston-actuating ram.

12 Claims, 5 Drawing Sheets

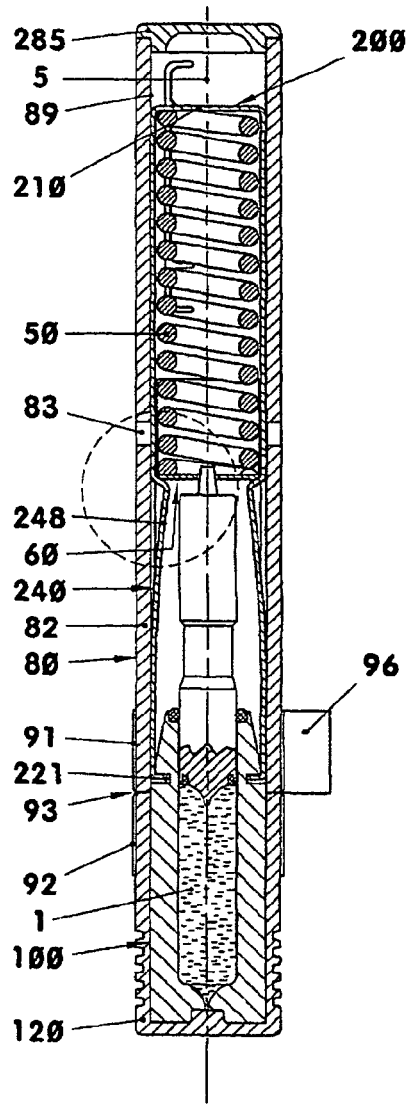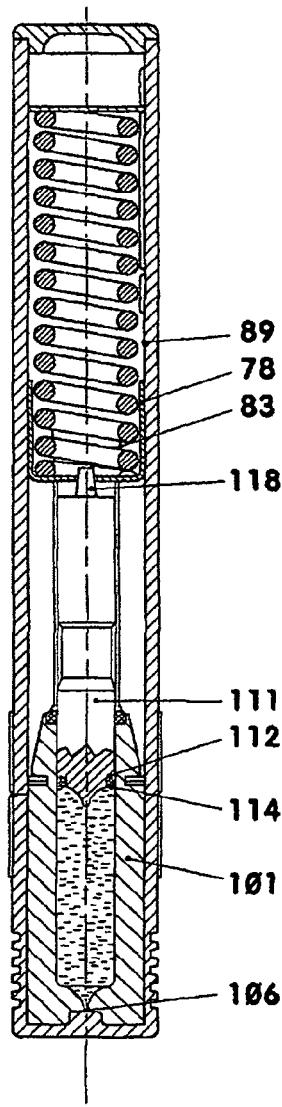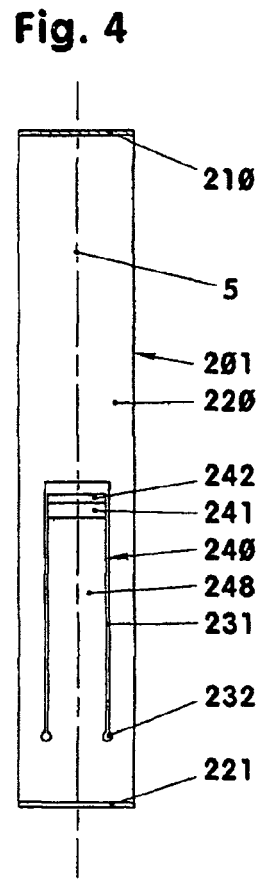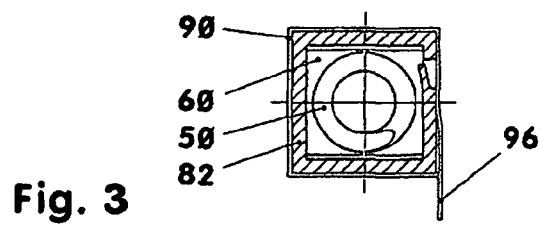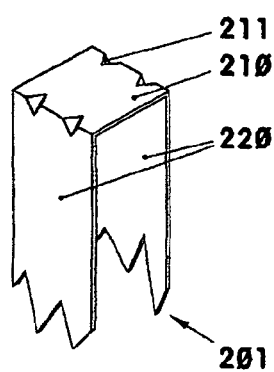

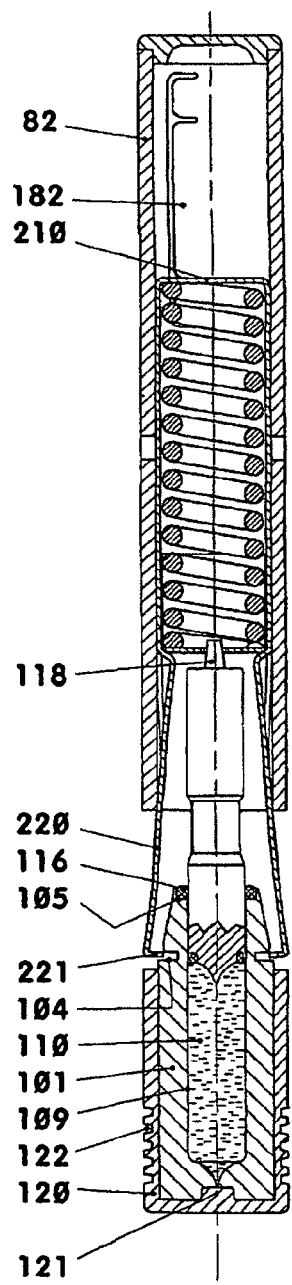
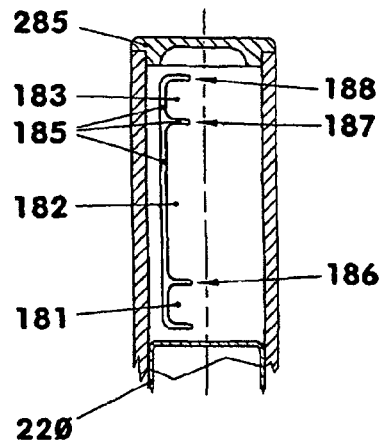
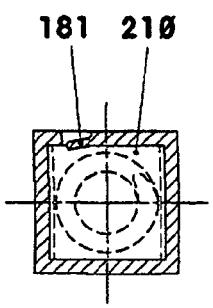
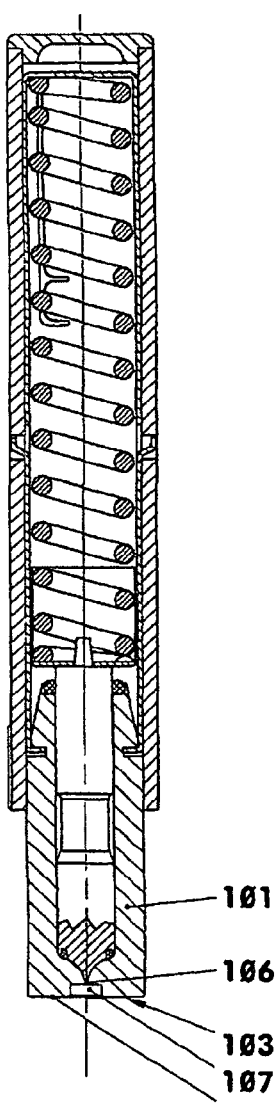
Fig. 6
Fig. 7
Fig. 8
Fig. 9

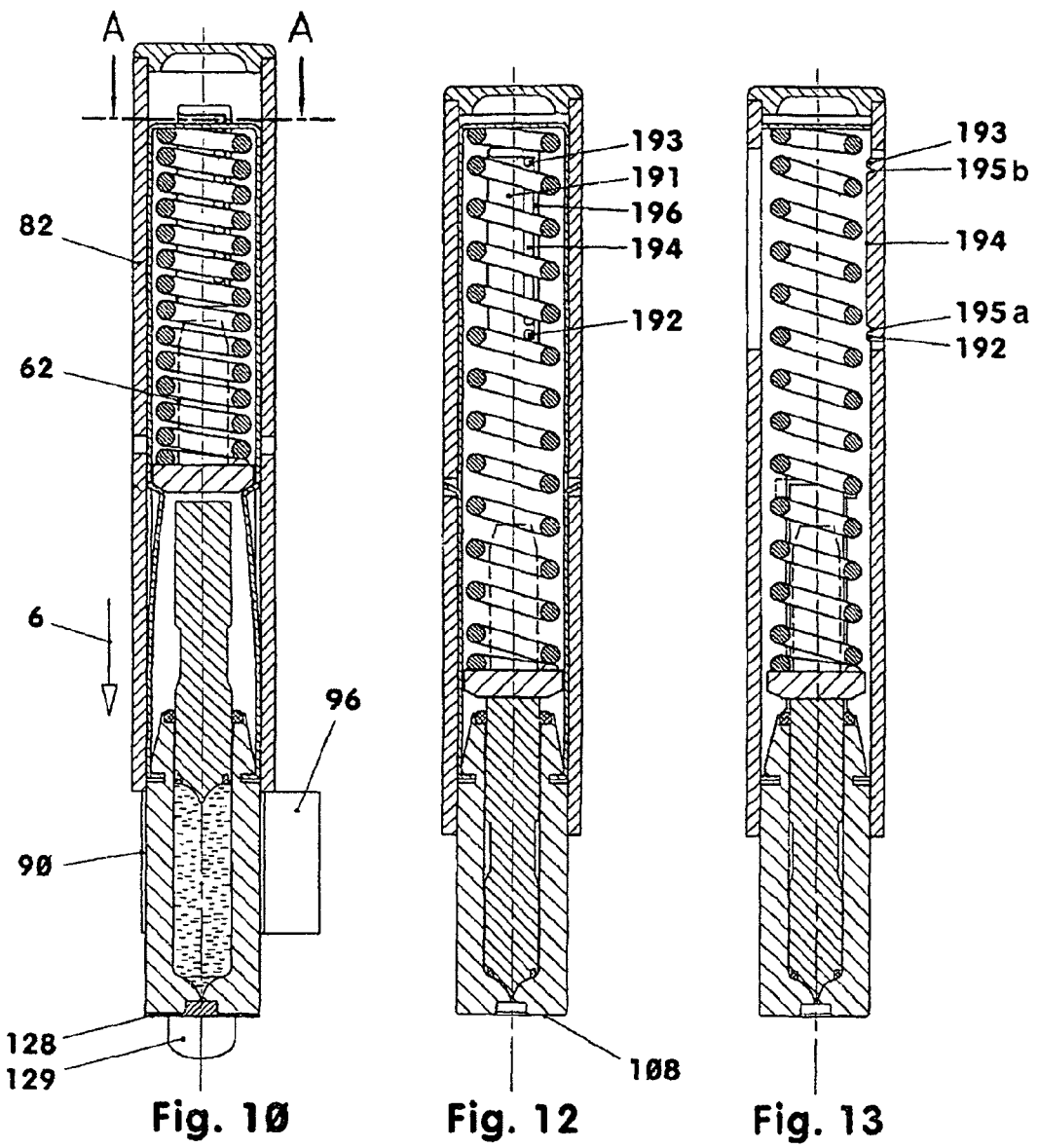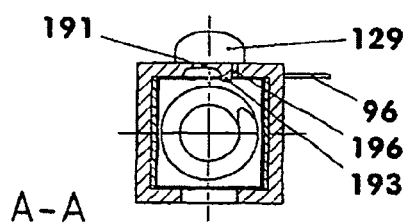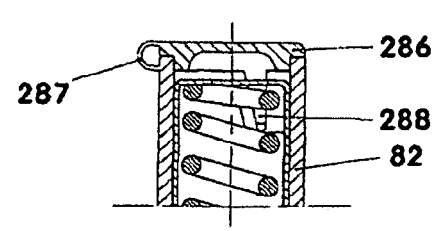

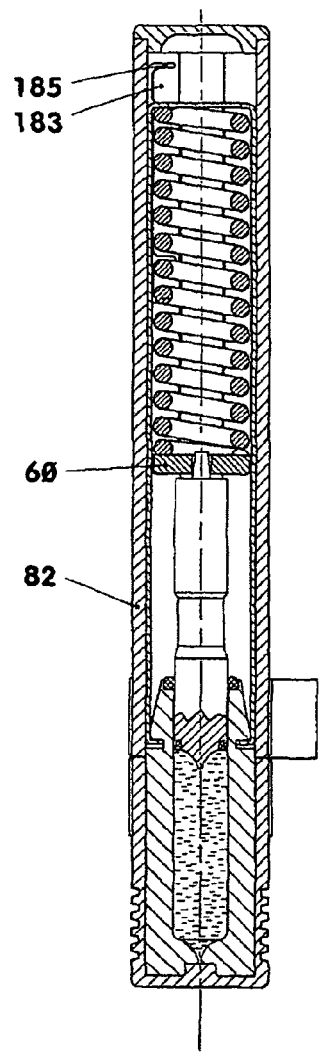
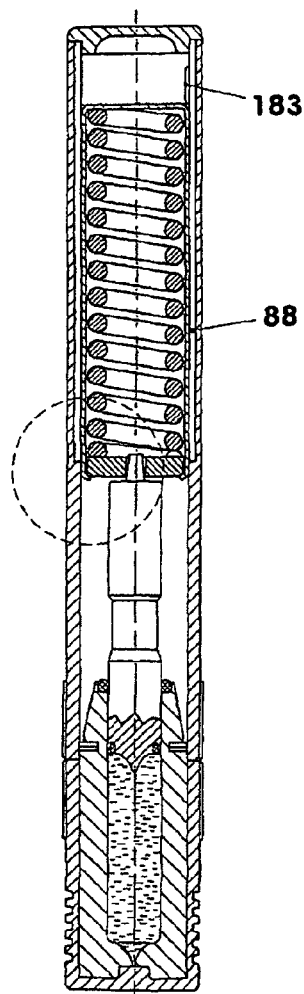
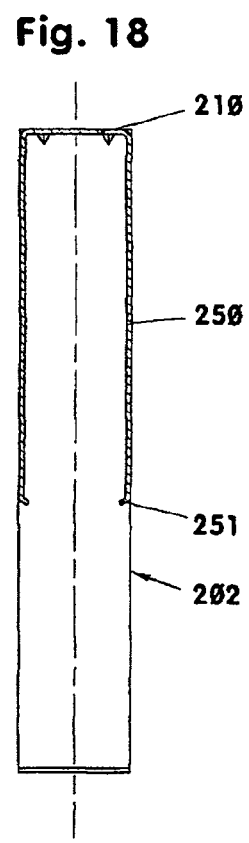
Fig. 15
Fig. 16
Fig. 18
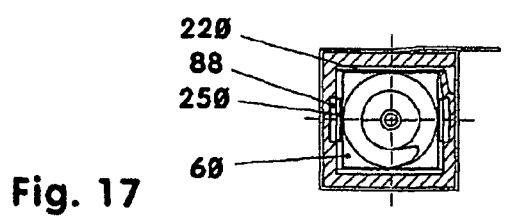
Fig. 17
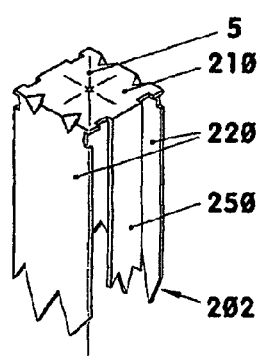
Fig. 19

SINGLE-USE INJECTOR HAVING A FLEXURALLY ELASTIC METAL HOUSING

CROSS-REFERENCE TO RELATED APPLICATION

This is a continuation-in-part application of pending international application PCT/EP2009/008612 filed Dec. 3, 2009 and claiming the priority of German Application No. 10 2008 063 519.7 filed Dec. 18, 2008.

BACKGROUND OF THE INVENTION

The invention relates to a disposable injector with a housing in which or on which are arranged, in each case at least in some areas, at least one mechanical spring energy reservoir, at least one cylinder/piston unit that can be filled at least temporarily with active substance, at least one piston-actuating ram and at least one trigger unit, wherein the piston-actuating ram is positioned between the spring energy reservoir and the piston of the cylinder/piston unit, wherein the spring energy reservoir comprises at least one pretensioned spring element, wherein the spring-loaded piston-actuating ram is supported on the housing via support rods or tension hooks, and wherein the contact zone situated between an individual support rod or tension hook and the piston-actuating ram represents a wedge gear pairing that forces the respective support rod or tension hook outwards.

DE 10 2007 031 630 A1 discloses, among other things, an injector of this type. With the exception of the mechanical spring of the spring energy reservoir, almost all the components of the injector are produced expensively from plastics by injection moulding. Components that are subject to high mechanical loads are additionally reinforced with glass fibres.

DE 10 2007 008 369 A1 discloses a one-way injector with a housing in which, or on which, —in each case at least over some part thereof—a mechanical spring energy store, at least one cylinder piston unit which at least at times is filled with an effective medium. At least one piston operating plunger and at least one release unit is arranged, wherein the spring-energy store comprises at least a pre-tensioned spring element and wherein at least part of the piston operating plunger is positioned between the spring energy store and the piston of the piston-cylinder unit. The spring-loaded piston operating plunger has at least one pull rod which has a support surface in the area of its rear end. At the support surface or surfaces, locking elements are supported on the housing whose locking position is secured by a release element which is secured in a blocking position. The release element has a release position which results in a release of the locking elements.

WO 2005/044 344 A1 discloses an arrangement for delivering an injectable product which arrangement includes a housing, a product container accommodated in the housing, a piston rod for moving the piston in the forward direction and a spring acting on the piston rod in the forward direction. The product container is supported so as to be moveable and includes a piston which is supported so as to be moveable in the forward direction for the emission of a product. The piston rod is supported, against the force of the spring, releasably in a holding position in a holding engagement so as to be releasable however. The spring extends in the holding position into the container.

Therefore, the problem addressed by the present invention is that of developing a disposable injector of modular design which, with a small overall size, comprises only a small number of components and, while being easy to handle and inexpensive to produce, ensures safe storage and operation.

SUMMARY OF THE INVENTION

The present invention provides a single-use injector comprising a housing (200) accommodating a mechanical spring energy reservoir (50), a cylinder/piston unit (100), a piston-actuating ram (60) and a trigger unit (80), the spring-loaded piston-actuating ram being supported on the housing via support rods (240) or draw hooks (250) and each contact zone between an individual support rod or draw hook and the piston-actuating ram representing a wedge gear pairing that forces the respective support rod or draw hook radially outwards. The housing of the injector consists of a thin-walled sheet metal part. Said sheet metal part has at least two limbs (220, 250) arranged parallel to each other. The sheet metal part has at least two pressure bars or at least two draw hooks the free ends of which are bent in an angular fashion to define a supporting section for the piston-actuating ram.

With the invention, a needleless disposable injector, for example, is made available whose piston-actuating ram is released upon triggering of the disposable injector. In order to pretension and hold the spring energy reservoir, the piston-actuating ram is held with a form fit via at least one support rod or tension hook arranged on the housing or integrated in the housing. The support rod(s) or tension hook(s) are held in their locked position, before use of the disposable injector, by a trigger element that surrounds the housing at least in some areas. In order to trigger the injector, the support rod(s) or tension hook(s) are released such that the piston-actuating ram, under the effect of the spring energy reservoir, can move at least approximately parallel to the centre line of the disposable injector, so as to ensure that the injection solution present in the cylinder of the cylinder/piston unit is discharged via at least one nozzle.

The housing is a simple, thin-walled sheet-metal part, possibly just a sheet-metal strip, which supports the mechanical or pneumatic spring of the spring energy reservoir together with a piston-actuating ram and a cylinder/piston unit in cooperation with the trigger element. The punched or cut sheet-metal part, bent several times, can be produced at very little cost from a ferrous material or a non-ferrous metal. Materials that have a high elastic limit, a high tensile strength and a high yield point are ideal. If appropriate, these can also be high-quality plastics and/or composite materials. Almost any material is suitable, even glass or ceramic.

BRIEF DESCRIPTION OF THE DRAWINGS

Further details of the invention will come clear from the following a number of illustrative embodiments represented schematically in the drawings, in which:

FIG. 1 shows a disposable injector with two support rods;
FIG. 2 shows the same as FIG. 1, but pivoted through 90 degrees;
FIG. 3 shows a cross section of FIG. 2;
FIG. 4 shows a longitudinal section of the sheet-metal strip;
FIG. 5 shows the upper area of the sheet-metal strip;
FIG. 6 shows a disposable injector in an intermediate stage of assembly;
FIG. 7 shows the upper area of the housing during assembly;
FIG. 8 shows a cross section of FIG. 7;
FIG. 9 shows the same as FIG. 1, but in the state when released and actuated;

FIG. 10 shows a disposable injector with two support rods in a simplified design, including a block-shaped ram;

FIG. 11 shows a cross section of FIG. 10;

FIG. 12 shows the same as FIG. 11, but in the state when released and actuated;

FIG. 13 shows the same as FIG. 12, but pivoted through 90 degrees;

FIG. 14 shows the upper area of the housing, with a housing lid formed integrally thereon;

FIG. 15 shows a disposable injector with two tension hooks and a block-shaped ram;

FIG. 16 shows the same as FIG. 15, but pivoted through 90 degrees;

FIG. 17 shows a cross section of FIG. 16;

FIG. 18 shows a longitudinal section of the sheet-metal part;

FIG. 19 shows the upper area of the sheet-metal part;

DETAILED DESCRIPTION OF THE PARTICULAR EMBODIMENTS

Figure 20:
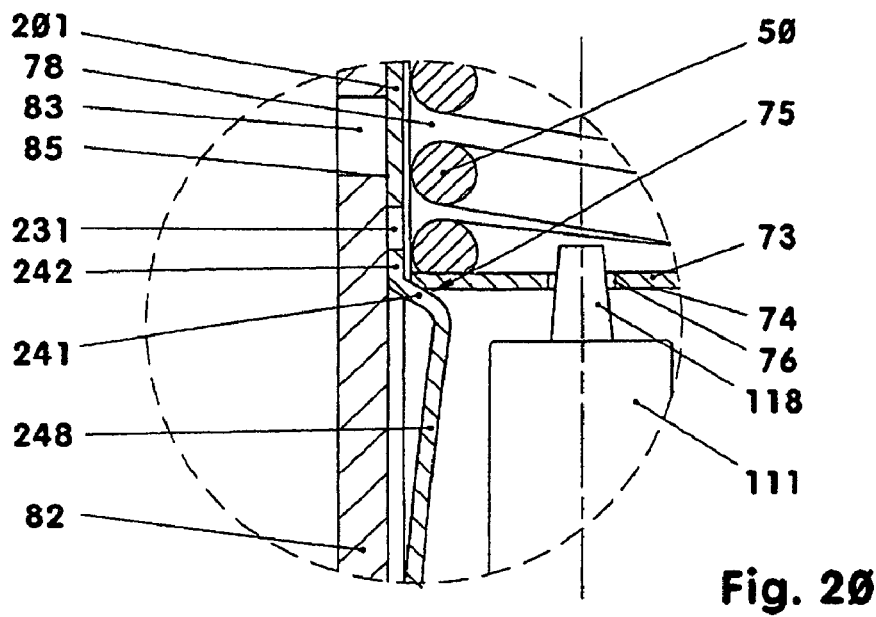
FIG. 20 shows an enlarged detail from FIG. 1.

FIG. 1 shows a disposable injector with a permanently charged spring energy reservoir. The disposable injector is composed of a housing (200), which is surrounded by a trigger element (82) and by a protective cap (120), of a cylinder/piston unit (100), which is prefilled with an injection solution for example, of a piston-actuating ram (60), and of a helical compression spring (50) as spring energy reservoir. The cylinder/piston unit (100) lies for the most part in the protective cap (120).

The housing (200) is a sheet-metal strip (201) that has been bent to form a "U", cf. FIG. 4. The sheet-metal strip (201), having a width of 18 millimeters for example, is approximately 240 millimeters when flat. The sheet-metal strip (201), produced if appropriate from spring steel, has a wall thickness of 0.5 millimeter, for example. The bent sheet-metal strip (201) is composed of a central end plate (210) and of two branches (220) protruding at least approximately perpendicularly from the latter. At their free ends, the branches (220), oriented at least approximately parallel to each other, are each bent inwards at an angle of 90 degrees to form a respective retaining element (221) there. The retaining elements (221) are, for example, 1.5 to 3 millimeters long and protrude towards each other. They form a plane that is oriented parallel to the end plate (210).

Instead of the hook-shaped retaining element (221), each branch (220) can be provided with a recess in which the cylinder of the cylinder/piston unit (100) can be suspended in each case by means of a pin.

At the transitions between the end plate (210) and the branches (220), two stiffening beads (211) are in each case pressed in according to FIG. 5. The stiffening beads (211) protrude so far into the end plate (210) that they additionally centre the last winding of the helical compression spring (50) on the end plate (210).

A support rod (240), with a width of 9 millimeters for example, is arranged in the lower half of each branch (220), cf. FIG. 4. The support rod (240) is formed by cutting out a U-shaped gap (231), with a width of 0.2 to 0.5 millimeter, for example. In the lower area of each branch (220), that is to say near the retaining elements (221), the gap (231) ends in bores (232) in order to minimize the notch stresses there. In contrast to the substantially plane branches (220), the support rod (240) is curved several times, cf. also FIG. 20. The support rod (240) is composed of a flexural beam (248), a supporting portion (241) and a bearing portion (242). The flexural beam (248) leads the tensioning force of the spring energy reservoir (50) into the branch (220) carrying it. The piston-actuating ram (60) lies on the supporting portion (241) when the disposable injector is in the untriggered state. By way of the bearing portion (242), the support rod (240) rests on the trigger element (82) over a large surface area.

The supporting portion (241), measuring approximately 1.5 to 3 millimeters in the longitudinal direction, cf. FIG. 20, encloses an angle of 110 to 115 degrees with the flexural beam (248). It is inclined by 60 degrees relative to the vertical. The bearing portion (242), which is 1 to 2 millimeters wide in the longitudinal direction, encloses an angle of 140° with the supporting portion (241). According to FIGS. 1 and 4, it lies over a large surface area on the trigger element (82). For example, the trigger element (82) has a ceramic lining in the contact area.

If appropriate, the elastic support rods (240) have, in the lower area, a longitudinal bead that runs at least approximately parallel to the centre line (5) and that serves to increase their resistance to buckling. The support rods (240) always yield resiliently outwards as elastic flexural beams (248) in order not to slow down the lengthening helical compression spring (50) during the triggering action.

The support rods (240) can also be replaced by tension hooks. The latter are likewise delimited from the respective branch (220) by a U-shaped slit. However, the bores (232) in this case lie near the end plate (210). The respective supporting portion of the tension hooks is designed, for example, like the supporting portions (251) of the tension hooks (250) from FIG. 18.

According to FIGS. 4 and 20, the piston-actuating ram (60) lies on the supporting portions (241) of the support rods (240). The piston-actuating ram (60) is in this case a sheet-metal strip that has been bent in a U-shape and that is composed of a middle part, the ram plate (73), and two guide branches (78). The ram plate (73) is oriented parallel to the end plate (210). The guide branches (78) protrude upwards at a right angle. The helical compression spring (50) sits between the guide branches (78). If appropriate, the guide branches (78) are stiffened relative to the ram plate (73) by stiffening beads, cf. the stiffening beads (211) of the sheet-metal strip (201) from FIG. 5.

According to FIG. 20, the ram plate (73), in the area in which it lies on the respective supporting portion (241) of the support rod (240), has a 20° bevel (75), for example, in order to ensure contact over a large surface area.

According to FIG. 1, the piston-actuating ram (60) has a width that is slightly smaller, that is to say by ca. 0.1 to 0.3 millimeter, than the normal distance between the two branches (220). Accordingly, the piston-actuating ram (60) is guided laterally on the branches (220). It will be seen in FIG. 2 that the guide branches (78) of the piston-actuating ram (60) are guided with play on the inner wall (89) of the trigger element (82).

According to FIGS. 1 to 3 and 20, among others, the ram plate (73) has a central bore (76) for additionally guiding the rear end of the piston (111) of the cylinder/piston unit (100).

The two support rods (240) subjected to pressure hold the piston-actuating ram (60), via the ram plate (73) thereof, in its pretensioned position, cf. FIGS. 1 and 20. For this purpose, the support rods (240) bear with their supporting portions (241) on the lower 20° bevel (75) of the ram plate (73). The size of the respective contact surface between the individual supporting portion (241) and the corresponding 20° bevel (75) is in the range of 5 to 20 mm$^2$.

The housing (200) made from sheet metal is for the most part surrounded by a trigger element (82) in which it sits and is able to slide. The trigger element (82) is here a square tube which is closed off at the rear end by a lid (285) and which is part of a trigger unit (80). The square tube (82), which is made of plastic, e.g. a polyamide, and which has a wall thickness of 1.5 to 2.5 millimeters for example, has two mutually opposite and, for example, rectangular windows (83) or apertures in its central area. The windows (83) have a width of 10.5 millimeters for example, and, in the longitudinal direction, i.e. parallel to the centre line (5), have a height of 3.75 millimeters. When the injector is triggered, they in each case receive the bearing portion (242) and the supporting portion (241) of the individual support rod (240), e.g. completely, cf. FIG. 9.

Three elastic locking tabs (181-183) protruding inwards by a few tenths of a millimeter are arranged in the rear area of the square tube (82) cf. FIGS. 7 and 8. The locking tabs (181-183) each have, for example, a rectangular shape. Their wall thickness corresponds to approximately 50% of the wall thickness of the square tube (82). They are delimited on three sides from the wall of the square tube (82) and from the nearest locking tab by gaps (185). The gaps (185) have a width of 0.5 millimeter, for example. The width corresponds to the wall thickness of the end plate (210). At the locations where two gaps (185) meet each other at right angles, the locking tabs (181-183) are rounded.

The eccentrically arranged locking tabs (181-183), formed integrally on the square tube, secure the position of the sheet-metal strip (201) at three locations (186-188). They protrude several tenths of a millimeter into the interior of the trigger element (82). The first location (186) is the gap between the front locking tab (181) and the middle locking tab (182). The end plate (210) is locked in the horizontal gap there, cf. FIG. 6, when the sheet-metal strip (201) is assembled, with the helical compression spring (50) clamped between the piston-actuating ram (60) and the end plate (210), for further intermediate storage.

The second location (187) is the gap between the middle locking tab (182) and the rear locking tab (183). According to FIGS. 1 and 2, the end plate (210) sits here in a disposable injector that has been fully assembled but not yet triggered. The locking of the end plate (210) in this gap prevents withdrawal of the housing (200) from the square tube (82), after removal of the protective cap (120). The third location (188) is the gap above the rear locking tab (183). The sheet-metal strip (201) locks itself in this position after the injector has been triggered, cf. FIG. 9. It is secured there against undesired disassembly of the injector that has then been used.

If appropriate, the respective upper corners of the locking tabs (181-183), i.e. the corners facing the lid (285), have a sharp edge, such that the sheet-metal strip (201) can only be pushed into the square tube (82). A movement in the opposite direction is then impossible.

Instead of the locking tabs (181-183), it is also possible to use a locking plate (191), cf. FIGS. 10 to 13. The locking plate (191) is a thin-walled, flexurally elastic plate which is integrated in the square tube (82). In an undeformed locking plate (191), the outer surface thereof ends flush with the outer face of the square tube (82), cf. FIG. 11. Towards the inside, the locking plate (191), which has been cut out with a C-shaped gap (196), has two locking stubs (192, 193) and a central locking web (194) along its longer inner edge. Between the locking stubs (192, 193) and the locking web (194) there is in each case a notch (195) whose width, at the notch base, corresponds to the wall thickness of the sheet-metal strip (201) or the wall thickness of the end plate (210). In the undeformed locking plate (191), the locking stubs (192, 193) and the locking web (194) protrude into the interior of the square tube (82). The site of the front notch (195a) corresponds as movement barrier to the first location (186), cf. FIG. 7, of the sheet-metal strip parking position, while the site of the rear notch (195b) represents the second sheet-metal strip parking position (187), cf. FIGS. 1, 2 and 7.

When the disposable injector has been fully assembled, the windows (83) and the gaps (185, 196) are covered to protect them from dust, for example, by an optionally elastic film which is permanently affixed by adhesive or shrink-fitted and which may, for example, be inscribed.

In the variants shown here, all the locking elements (181-183; 192-194) are arranged on the trigger element (82). They fix the position of the end plate (210) relative to the trigger element (82) in some cases temporarily and in some cases permanently. It is also conceivable for the locking elements (181-183; 192-194) to be replaced by, for example, a cam-like locking element arranged on the housing (200). This element would then engage in corresponding cuttings in the trigger element (82) in order to provide comparable locking positions.

At the rear end, the square tube (82) is closed off by a lid (285). The lid (285) is connected to the trigger element (82), for example, by adhesive bonding, welding, locking or compression. If appropriate, the lid is also formed integrally on the trigger element (82).

FIG. 14 shows a lid (285) which is formed integrally on the square tube (82) via a film hinge (287). In the folded-open state, it is produced together with the square tube (82) by injection moulding. A locking hook (288) protrudes downwards from the lid (285). The locking hook (288) secures the sheet-metal strip (201) in the position shown in FIG. 10.

In this illustrative embodiment, the cylinder/piston unit (100) comprises a transparent cylinder (101) which is filled with an injection solution (1) or a solvent, e.g. water for injection, and in which, according to FIG. 1, a piston (111) sits in its rear position.

The cylinder (101) is, for example, a thick-walled pot. The cylinder bore is, for example, cylindrical or frustoconical. In the centre of the bore, of which the cylinder base is adapted at least approximately to the contour of the front end face of the piston (111), there is a short cylindrical, nozzle-like bore (106). The diameter thereof is approximately 0.1 to 0.5 millimeter. This bore (106) is one to five times as long as its diameter. It ends in a cylindrical recess (107) in the outer end face (103) at the bottom of the cylinder (101), cf. FIG. 9. If appropriate, it is also possible to arrange two or more nozzle-like bores (106) in the base of the cylinder (101).

Around the recess (107), an adhesive ring (108) firmly adheres to the end face (103). The adhesive ring (108) covers almost the whole of the end face (103).

The spatial outer contour of the cylinder (101) has, for example, a square configuration in the illustrative embodiment. However, it can also be cylindrical. In the central area of the cylinder, the cross section of the outer contour, oriented transversely with respect to the centre line (5), is a square surface with a central bore. The cross section is dimensioned such that the cylinder (101) slides with slight play in the interior of the square tube (82).

In the upper quarter directed towards the square tube (82), the cylinder (101) has, in its outer contour, a for example circumferential retaining notch (104) with, for example, a rectangular notch cross section. Above the retaining notch (104), the cylinder (101) narrows in a truncated pyramid shape. The angle enclosed by mutually opposite pyramidal surfaces is, for example, 20 to 30 degrees. If appropriate, the retaining notch (104) can also be composed simply of two mutually opposite single notches.

The cylinder (101) has a cylinder inner wall (109) which, in the area of the rear face of the cylinder, ends in an annular groove (105) for receiving a sealing element (116).

At its front and at least approximately conically shaped end face, the piston (111) lying in the cylinder (101) has an axial annular groove (112) for receiving a sealing ring (114) or a permanently elastic sealing compound. In its central area, the piston (111) has a waist, and, at its rear end, a central frusto-conical pin (118), which engages with play in the bore (76) of the ram plate (73).

The piston (111) and the sealing element (116) close off the filled interior (110) of the cylinder in a sterile manner.

According to FIG. 10, the cylindrical recess (107) in the bottom end face (103) of the cylinder (101) is closed off by a protective film (128), for example. The protective film (128) adheres over an adhesive ring (108) on the end face (103). It has a lateral pull-off tab (129). In the central area of the protective film (128), there is an elastic stopper which adheres firmly to the protective film (128) and which sealingly fills the hollow space of the recess (107).

As an alternative to this, a pot-shaped protective cap (120) is fitted onto the cylinder (101) from underneath, as shown in FIGS. 1 and 2, among others. In geometrical terms, the one-piece protective cap (120) is composed in principle of five plane walls, and it encloses the cylinder (101) laterally with slight play. Its upper and, for example, plane end face makes contact with the front end face of the trigger element (82) in the form of a square tube. The outer wall of the protective cap (120) is profiled or structured so as to make it easier to pull off from the cylinder (101). In the illustrative embodiment, a groove profile (122) is used.

The base of the protective cap (120) has a stopper (121) which engages sealingly in the recess (107) of the cylinder (101). The protective cap (120) adheres to the cylinder (101) via the adhesive ring (108). The latter has a substantially greater adherence to the cylinder (101) than it has to the base of the protective cap (120). In order to further ensure the difference in adherence, the base is optionally provided with a profile or a shoulder, such that the contact surface to the adhesive ring (108) is smaller than the contact surface between the adhesive ring (108) and the end face (103) of the cylinder.

The helical compression spring (50) sits pretensioned between the ram plate (73) and the end plate (210) of the sheet-metal strip (201). The spring force is transmitted to the support rods (240) via the ram plate (73). Because of the inclination of the bevel (75) of the ram plate (73), the support rods (240) are forced radially outwards like a wedge gear, cf. FIG. 20. The bevels (75) make contact with the inclined supporting portions (241) of the support rods (240). The bearing portions (242) lie at least virtually flat on the inner wall of the square tube (82). The square tube (82) thus permanently supports the radial force caused by the wedge gear.

According to FIGS. 1 and 2, the square-tube-shaped trigger element (82) and the protective cap (120) touch at their end faces. As a tamper-evident seal, this area is additionally enclosed by a banderole (90) as safety element. The banderole (90), which can be torn off or separated, is, for example, a paper strip or film strip that is coated on one side with an adhesive. The film strip surrounds once, for example, in a single layer, the combination of trigger element (82) and protective cap (120). It temporarily affixes the parts (82) and (120). To prime the injector or remove the protective cap (120), in preparation for using the injector, the banderole (90) is pulled off or separated in such a way that the adhesive connection between the trigger element (82) and the protective cap (120) is undone. For this purpose, in the illustrative embodiment, the tear-off tab (96) lying in the area of the trigger element (82) is gripped and the banderole (90) is thus wound off, e.g. in sections. In doing so, the banderole (90) tears at a defined and, for example, rectilinear predetermined breaking point (93), which lies exactly in the area of the end faces. Consequently, during priming, only that part (91) of the banderole (90) bearing on the trigger element (82) is removed.

FIGS. 6 and 7 show the injector in an intermediate stage of assembly. The assembly procedure first entails joining the helical compression spring (50) to the piston-actuating ram (60) and the sheet-metal strip (201). To do so, the helical compression spring (50) is fitted into the already shaped sheet-metal strip (201) in such a way that one end of the spring comes to bear on the end plate (210). The stirrup-like piston-actuating ram (60) is pushed onto the other end of the spring. Then, with the aid of an assembly device that guides the helical compression spring (50) on the outside or inside, the sheet-metal strip (201) is pushed together between the end plate (210) and the piston-actuating ram (60), counter to the spring action, to such an extent that the bevels (75) of the end face (74) come to lie behind the supporting portions (241). In doing so, the bearing portions (242) resting laterally on the piston-actuating ram (60) facilitate the assembly procedure.

The combination of the tensioned spring (50), of the sheet-metal strip (201) and of the piston-actuating ram (60), still tensioned in the assembly device, is now inserted from underneath into the square tube (82). The insertion procedure finishes when the end plate (210) locks in the gap (185) situated between the locking tabs (181) and (182). In this position (186), cf. FIG. 6, the free ends of the branches (220) protrude downwards from the square tube (82).

In a further assembly stage, the filled cylinder/piston unit (100) is inserted, with the guide pin (118) of the piston (111) to the front, into the square tube (82) in such a way that, on the one hand, the guide pin (118) engages in the bore (76) of the piston-actuating ram (60) and, on the other hand, the retaining elements (221) of the branches (220) engage in the retaining notch (104) of the cylinder (101). Starting from this position, the square tube (82) is pushed further over the sheet-metal strip (201) until the end plate (210) locks in the gap (185) situated between the locking tabs (182) and (183). In this process, the retaining elements (221) engage securely in the retaining notch (104) and thus fix the cylinder/piston unit (100) in the square tube (82). Compared to the assembly stage shown in FIG. 1, all that remains to be done is to apply the tamper-evident seal (90) and cover the windows (83) and the gaps (185, 196) by means of an inscribed film.

FIGS. 10 to 13 show a simplified variant compared to FIGS. 1 to 9. It differs in seven points, among others. First, the support rods (240) do not have separate bearing portions, cf. FIGS. 10 and 12 in contrast to FIG. 20. Second, the piston-actuating ram (60) is just a square plate without a bore and with two or four bevels (75) on its lower end face (74). If appropriate, a guide pin (62), here indicated by broken lines, is secured or integrally formed on the upper end face of the square plate. Third, the piston (111) does not have a guide pin on its rear end face. Fourth, the trigger element (82) has a locking plate (191) instead of the locking tabs (181-183), cf. FIG. 7. Fifth, instead of the protective cap (120), cf. FIG. 1, the cylinder (101) only has a protective film (128), cf. FIGS. 10 and 11. Sixth, the banderole (90) is only wound around the cylinder (101). However, the film of the banderole (90) has a sufficient wall thickness to ensure that it securely blocks a movement of the trigger element (82) in the direction of triggering (6). Seventh, the trigger element (82) has, for example, an integrally formed lid (285) according to FIG. 14.

A third variant of a disposable injector is shown in FIGS. 15 to 19. This injector does not have a sheet-metal strip (201) as its housing, but instead a sheet-metal cross (202), cf. FIGS. 18 and 19. FIG. 19 shows the upper area of the already shaped sheet-metal cross (202). Here, the sheet-metal cross (202) has the already known end plate (210), on which are arranged two wide and long branches (220) and, offset by an angle of 90 degrees about the centre line (5), two narrow and short branches (250). The stated size relationships are given only by way of example.

The long and wide branches (220) have the role of holding the cylinder (101) via the retaining elements (221), cf. also FIGS. 1 and 2. However, in FIGS. 15 to 19, these branches (220) do not have support rods.

The short and narrow branches (250) serve as tension hooks and replace the support rods. At their free and, according to FIG. 18, lower ends, the tension hooks (250) shown here each have a supporting portion (251), which is obtained by simply bending the end of the tension hook inwards, e.g. by an angle of 60 degrees. With the spring energy reservoir (50) tensioned, the here plate-shaped piston-actuating ram (60) lies with its bevels (75) on the supporting portions (251).

Figure 21:
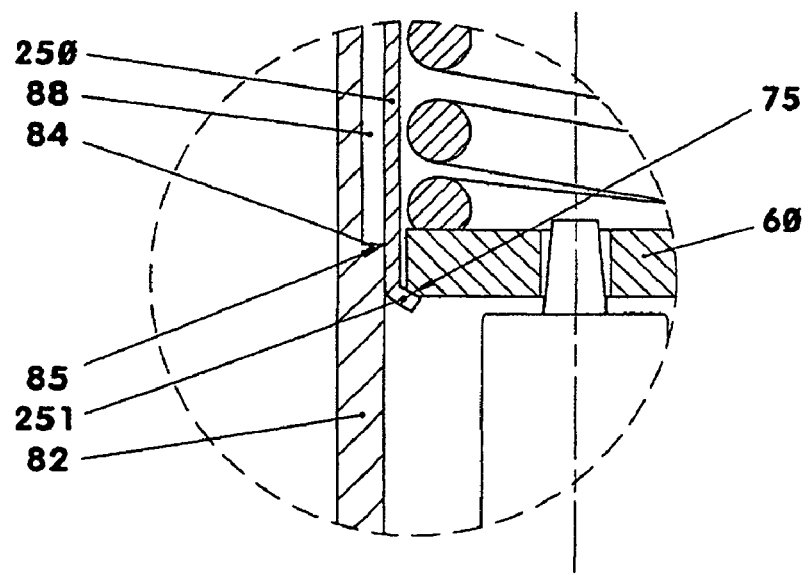
FIG. 21 shows an enlarged detail from FIG. 16.

According to FIGS. 15, 16 and 21, the piston-actuating ram (60) is a flat plate with, for example, a square or rectangular end face, cf. FIG. 17.

With the spring energy reservoir (50) tensioned, the tension hooks (250) bear on the inner wall of the trigger element (82) below the edges (85) belonging to the longitudinal grooves (88). Here too, the supporting portions (251) and the bevels (75) form a wedge gear that forces the tension hooks (250) outwards. In the dismantled state, the resiliently elastic tension hooks (250) jut outwards. In this way, they yield outwards after the injector is triggered, and independently of the action of the wedge gear, so as not to impede the helical compression spring (50) in its change of length.

To allow the tension hooks (250) to be forced outwards when the injector is triggered, the trigger element (82), in this case again in the shape of a square tube, for example, requires the two aforementioned and mutually facing longitudinal grooves (88) on the inner wall (89), cf. FIGS. 16 and 17. Each longitudinal groove (88) ends, in the central area of the trigger element (82), in a return flank (84), cf. FIG. 21. As a result of the movement of the trigger element (82) when triggered, the edges (85) arrive below the supporting portions (251) of the tension hooks (250), as a result of which these retreat into the longitudinal grooves (88).

Because of the arrangement of the longitudinal grooves (88) in the square tube (82), the locking tabs (181-183), via which the sheet-metal cross (202) is locked in various positions, are shifted in the direction of the inner edge of the next corner.

Instead of the described housing-like sheet-metal cross (202), it is also possible to use a sheet-metal star with six, eight or more branches. For example, a sheet-metal star has an octagonal end plate (210), from which four branches with retaining elements (221) and four other branches with supporting portions (251) are arranged at least approximately perpendicularly. The retaining elements (221) and the supporting portions (251) alternate with each other. The piston/cylinder unit (100) and the trigger element (82) then also have octagonal cross sections, for example. The sheet-metal cross or the sheet-metal star can also be constructed from individual sheet-metal strips, with the sheet-metal strips being connected to one another in the area of the end plate (210), for example by welding or riveting.

To prepare the disposable injector shown in FIGS. 1 to 9 for use, it is first primed by detaching the tear-off tab (96) and the rear banderole section (91). The protective cap (120) is then withdrawn from the cylinder/piston unit (100). The injector, with the adhesive ring (108) facing forwards, is then positioned on the injection site. In doing this, the disposable injector is held in the fist by way of the square tube (82). The thumb of the hand holding the injector rests, for example, on the lid (285), e.g. as when holding a pen.

The square tube (82) is now moved in the direction of the cylinder/piston unit (100). In this process, the trigger element (82) slides linearly down the sheet-metal strip (201), that is to say in the direction of the injection site. The bearing portions (242) of the support rods (240) slip over the edge (85) and, under the force of the spring element (50), spring radially outwards into the windows (83). The supporting portions (241) release the piston-actuating ram (60). The latter shoots downwards unimpeded. In doing so, the end face (74) of the ram plate (73) strikes the end face of the piston (111) previously situated a few tenths of a millimeter or a few millimeters away. The piston (111) forces the injection solution or medicament (1) through the nozzle (106), e.g. initially at $300 \times 10^5$ Pa, until the cylinder (101) is emptied, cf. FIG. 9. The injection procedure is completed with the discharging of the injection solution (1).

The illustrative embodiments show injectors in which the branches (220, 250) of the housing are oriented at least approximately parallel to each other in respective pairs (an angle deviation of ±2 degrees is permissible). The branches (220, 250) lie in parallel planes, wherein the planes, seen in the cross section of the injector, form the mutually opposite sides of a rectangle. The plane of the cross section of the injector lies perpendicular to the centre line (5). These sides can also belong to a rhombus, a parallelogram, a trapezoid or an oblique quadrilateral.

In addition, the branches (220, 250) and the pressure rods (240) are each of the same length in respective pairs. This is not absolutely necessary. For example, the pressure rods (240) can be of different lengths if the bearing surfaces of the piston-actuating ram (60) and the windows (83) are correspondingly offset.

LIST OF REFERENCE SIGNS 1 injection solution; medicament
5 centre line of injector, longitudinal direction
6 direction of triggering movement of (82), downward movement in direction of arrow
50 spring element, helical compression spring, spring energy reservoir
60 piston-actuating ram
62 guide pin
73 ram plate
74 end face, lower
75 bevel, 20° bevel
76 bore
78 guide arm
80 trigger unit
82 trigger element, square tube
83 windows, apertures
84 return flank
85 edge, sharp-edged
88 longitudinal grooves
89 inner wall
90 tamper-evident seal, banderole, safety element
91 rear banderole section, on (82); part
92 front banderole section, on (120)

93 predetermined break, perforation
96 tear-off tab
100 cylinder/piston unit
101 cylinder
103 end face
104 retaining notch
105 annular groove
106 bore, nozzle
107 recess in the end face
108 adhesive ring
109 inner wall of cylinder
110 interior of cylinder
111 piston
112 annular groove
114 sealing ring, seal
116 sealing element in (105)
118 guide pin
120 protective cap
121 stopper
122 groove profile
128 protective film, adhesive seal
129 pull-off tab
181 locking tab, front; locking element
182 locking tab, middle; locking element
183 locking tab, rear; locking element
185 gaps
186 1st location
187 2nd location
188 3rd location
191 locking plate
192,193 locking stub; locking element
194 locking web; locking element
195a front notch
195b rear notch
196 gap, C-shaped
200 housing; sheet-metal part, thin-walled
201 sheet-metal strip; sheet-metal part
202 sheet-metal cross; sheet-metal part
210 end plate
211 beads, stiffening beads
220 branch, long and wide
221 retaining elements
231 gap, U-shaped
232 bores
240 support rods, pressure rods
241 supporting portion
242 bearing portion
248 flexural beam
250 tension hook; branch, short and narrow
251 supporting portion
285 lid
286 lid with film hinge
287 film hinge
288 locking hook

What is claimed is:

1. In combination with a one-way disposable injector with a housing (200) in which or on which are arranged, in each case at least in some areas, at least one mechanical spring energy reservoir (50), at least one cylinder/piston unit (100) that can be filled at least temporarily with active substance, at least one piston-actuating ram (60) and at least one trigger unit (80), the piston-actuating ram (60) is positioned between the spring energy reservoir (50) and the piston (111) of the cylinder/piston unit (100),
the spring energy reservoir comprises at least one pretensioned spring element (50), and
the spring-loaded piston-actuating ram (60) is supported on the housing (200) via support rods (240) or tension hooks (250), and wherein the contact zone situated between an individual support rod (240) or tension hook (250) and the piston-actuating ram (60) represents a wedge gear pairing that forces the respective support rod (240) or tension hook (250) outwards, the improvement which comprises:
the housing (200) is made from a thin-walled sheet-metal part (201, 202),
the sheet-metal part (201, 202) has at least two branches (220, 250),
the branches (220) each have, at the free ends thereof, an angled retaining element (221) or a recess as a means of receiving the cylinder (101) of the cylinder/piston unit (100),
the sheet-metal part (201, 202) has at least two pressure rods (240) or at least two tension hooks (250), the free ends of which are each bent at an angle to form a supporting portion (241, 251) for the piston-actuating ram (60), and
the at least one trigger unit (80) comprises at least one trigger element (82) which is slidably arranged on the housing (200), wherein the at least one trigger element (82) has windows (83) or longitudinal grooves (88) which accommodate the supporting portions (241) of the support rods (240) or the support portions (251) of the tension hooks (250) after the release of the one-way disposable injector.

2. The disposable injector according to claim 1, wherein the housing (200) is made from a sheet-metal strip (201), the sheet-metal strip (201) is bent in a U-shape to form two branches (220),
the sheet-metal strip (201) has, at both free ends, inwardly angled retaining elements (221) as a bearing for the piston-actuating ram (60),
a support rod (240) or a tension hook (250) is worked into at least one branch (220) and is bent at an angle, at its free end, to form a supporting portion (241, 251) for the piston-actuating ram (60).

3. The disposable injector according to claim 1, wherein the sheet-metal part (201, 202) is made from a spring steel.

4. The disposable injector according to claim 1, wherein the trigger element (82) is a square tube surrounding the sheet-metal part (201, 202).

5. The disposable injector according to claim 4, wherein the trigger element (82) has, at least at two locations (186, 187), locking notches for temporarily securing the position of the sheet-metal part (201, 202).

6. The disposable injector according to claim 1, wherein the piston-actuating ram (60) is a flat plate (73) with a rectangular surface area or is made from a sheet-metal strip (73, 78) bent in a U-shape.

7. The disposable injector according to claim 1, wherein the plate (73) or the sheet-metal strip (73, 78) has a central bore (76) in its area situated transverse to the centre line (5) of the injector.

8. The disposable injector according to claim 1, wherein the piston (111) of the cylinder/piston unit (100) has a guide pin (118) on its rear face.

9. The disposable injector according to claim 1, wherein the piston-actuating ram (60), together with each individual support rod (240), forms a spline gear in which an axial spring force direction is converted into a radial supporting force direction.

10. The disposable injector according to claim 1, wherein the individual support rod (240) is in each case formed as a monolithic portion of the housing (200) and represents an elastic flexural beam (248).

11. The disposable injector according to claim 1, wherein the trigger element (82), in combination with the housing (200) and with a tear-off banderole (90) secured thereon, forms a trigger unit (80).

12. The disposable injector according to claim 5, wherein the trigger element (82) further comprises tabs (181, 182, 183), the tabs (181, 182, 183) are formed as monolithic portions of the trigger element (82), the locking notches at the at least two locations (186, 187) are formed between the tabs (181, 182, 183).

* * * * *